United States Patent [19]

Schallner et al.

[11] Patent Number: 5,389,599
[45] Date of Patent: Feb. 14, 1995

[54] SUBSTITUTED HETEROCYCLYLTRIAZINEDIONES

[75] Inventors: Otto Schallner, Monheim; Klaus Lürssen; Robert R. Schmidt, both of Bergisch Gladbach; Hans-Joachim Santel, Leverkusen; Christoph Erdelen, Leichlingen, all of Germany

[73] Assignee: Bayer Aktiengesellschaft, Leverkusen, Germany

[21] Appl. No.: 986,639

[22] Filed: Dec. 8, 1992

[30] Foreign Application Priority Data

Dec. 18, 1991 [DE] Germany ............... 4141721

[51] Int. Cl.⁶ ............ C07D 403/04; A01N 43/66
[52] U.S. Cl. ................ 504/230; 544/212; 544/223
[58] Field of Search ............... 544/212, 223; 504/230

[56] References Cited

U.S. PATENT DOCUMENTS

| 4,035,365 | 7/1977 | Kay | 71/93 |
| 4,105,433 | 8/1978 | Collins et al. | 71/93 |

FOREIGN PATENT DOCUMENTS

| 2506603 | 9/1975 | Germany . |
| 2603180 | 8/1976 | Germany . |

OTHER PUBLICATIONS

Kay et al., Chemical Abstracts, vol. 89, entry 101868g (1978).
Bigg et al., Chemical Abstracts, vol. 86, entry 29700q (1977).
Kay, Chemical Abstracts, vol. 84, entry 26854r (1976).
Seckinger, Chemical Abstracts, vol. 78, entry 147924y (1973).
Chemical Abstracts, vol. 95, 1981, Columbus, Ohio, US; Abstract No. 150711hk "Triazine-2,6-dione derivatives", p. 677.

*Primary Examiner*—John M. Ford
*Attorney, Agent, or Firm*—Sprung Horn Kramer & Woods

[57] ABSTRACT

The invention relates to new substituted heterocyclyltriazinediones of the general formula (I)

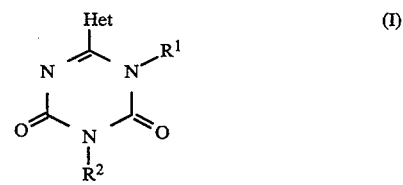

in which
R¹ represents hydrogen or an in each case optionally substituted radical from the series comprising alkyl, alkenyl, alkinyl or cycloalkyl,
R² represents an in each case optionally substituted radical from the series comprising alkyl, alkenyl, alkinyl or cycloalkyl and
Het represents an N-linked, optionally substituted unsaturated nitrogen-containing heterocycle which can optionally contain further hetero atoms, a plurality of processes for their preparation, and their use as herbicides and insecticides.

11 Claims, No Drawings

SUBSTITUTED HETEROCYCLYLTRIAZINEDIONES

The invention relates to new substituted heterocyclyltriazinediones, to a plurality of processes for their preparation, and to their use as herbicides and insecticides.

It has been disclosed that certain substituted triazinediones such as, for example, the compound 1-isopropyl-4-[N-(2,2-dimethylpropyl)-acetamido]-1,3,5-(3H)-triazine-2,6-dione, have herbicidal properties (compare, for example, DE 2,603,180).

However, the herbicidal activity of these previously known compounds against problem weeds as well as their compatibility with important crop plants is not entirely satisfactory in all fields of application.

New substituted heterocyclyltriazinediones of the general formula (I)

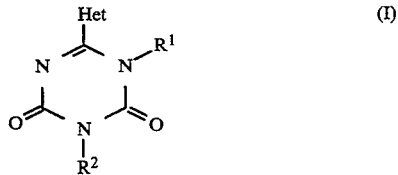

in which
R¹ represents hydrogen or an in each case optionally substituted radical from the series comprising alkyl, alkenyl, alkinyl or cycloalkyl,
R² represents an in each case optionally substituted radical from the series comprising alkyl, alkenyl, alkinyl or cycloalkyl and
Het represents an N-linked, optionally substituted unsaturated nitrogen-containing heterocycle which can optionally contain further hetero atoms,
have been found.

Depending on the nature of the substituents, the compounds of the formula (I) can, if appropriate exist in the form of geometric and/or optical isomers or isomer mixtures of various compositions. The invention claims the pure isomers as well as the isomer mixtures.

Further, it has been found that the new substituted heterocyclyltriazinediones of the general formula (I) are obtained when a) 4-alkylthiotriazinediones of the formula (II)

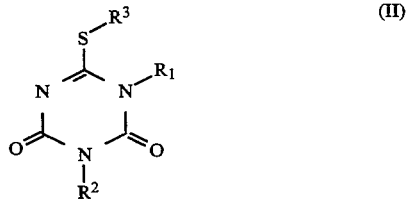

in which
R¹ and R² have the abovementioned meaning and
R³ represents alkyl,
are reacted with heterocycles of the formula (III)

Het—H    (III)

in which
Het has the abovementioned meaning, if appropriate in the presence of a diluent, and, if appropriate, b) the resulting substituted heterocyclyltriazinediones of the formula (I)

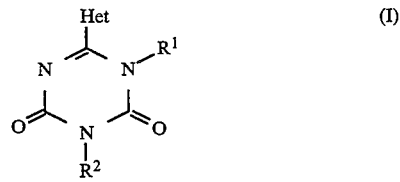

in which
R¹, R² and Het have the abovementioned meaning, are subsequently substituted in the heterocyclyl moiety of the substituent Het by electrophilic reagents, if appropriate in the presence of a diluent and if appropriate in the presence of a reaction auxiliary.

Finally, it has been found that the new substituted heterocyclyltriazinediones of the general formula (I) have herbicidal and insecticidal properties.

Surprisingly, the substituted heterocyclyltriazinediones of the general formula (I) according to the invention show considerably better herbicidal activity against problem weeds combined with an equally good compatibility with important crop plants compared with the substituted triazinediones known from the prior art such as, for example, the compound 1-isopropyl-4-[N-(2,2-dimethylpropyl)-acetamido]-1,3,5-(3H)-triazine-2,6-dione, which are similar compounds chemically and from the point of view of their action.

Formula (I) provides a general definition of the substituted heterocyclyltriazinediones according to the invention. Preferred compounds of the formula (I) are those in which R¹ represents hydrogen, or represents an in each case straight-chain or branched radical from the series comprising alkyl having 1 to 12 carbon atoms, alkenyl having 2 to 6 carbon atoms, alkinyl having 2 to 6 carbon atoms, alkoxyalkyl or alkylthioalkyl, each of which has 1 to 6 carbon atoms in the individual alkyl moieties, halogenoalkyl having 1 to 6 carbon atoms and 1 to 13 identical or different halogen atoms, halogenoalkenyl having 2 to 6 carbon atoms and 1 to 11 identical or different halogen atoms, halogenoalkinyl having 2 to 6 carbon atoms and 1 to 9 identical or different halogen atoms, or represents cycloalkyl which has 3 to 8 carbon atoms and which is optionally monosubstituted or polysubstituted by identical or different substituents, suitable cycloalkyl substituents being: halogen, straight-chain or branched alkyl having 1 to 4 carbon atoms or straight-chain or branched halogenoalkyl having 1 to 4 carbon atoms and 1 to 9 identical or different halogen atoms, R¹ furthermore represents arylalkyl, aryloxyalkyl, arylthioalkyl or heteroarylalkyl, each of which has 1 to 6 carbon atoms in the straight-chain or branched alkyl moiety and each of which has 6 to 10 carbon atoms in the aryl moiety, or 2 to 9 carbon atoms and 1 to 4 hetero atoms—in particular nitrogen, oxygen and/or sulphur—in the heteroaryl moiety, and each of which is optionally monosubstituted or polysubstituted if appropriate in the aryl, or heteroaryl, moiety by identical or different substituents, suitable aryl, or heteroaryl, substituents in each case being: halogen, cyano, nitro, in each case straight-chain or branched alkyl, alkoxy or alkylthio, each of which has 1 to 4 carbon atoms, in each case straight-chain or branched halogenoalkyl, halogenoalkoxy, halogenoalkylthio, each of which has 1 to 4 carbon atoms and 1 to 9 identical or different halogen atoms, in each case straight-chain or branched alkoxycarbonyl or alkoximinoalkyl, each of which has 1 to 4 carbon, atoms in the individual alkyl moieties, and phenyl which is optionally monosubstituted or polysubstituted by identical or different substituents from the series comprising halogen and/or straight-chain or branched alkyl having 1 to 4 carbon atoms, $R^2$ represents an in each case straight-chain or branched radical from the series comprising alkyl, alkoxy or alkylthio, each of which has 1 to 8 carbon atoms, alkenyl having 2 to 6 carbon atoms, alkinyl having 2 to 6 carbon atoms, halogenoalkyl having 1 to 6 carbon atoms and 1 to 13 identical or different halogen atoms, halogenoalkenyl having 2 to 6 carbon atoms and 1 to 9 identical or different halogen atoms, halogenoalkinyl having 2 to 6 carbon atoms and 1 to 9 identical or different halogen atoms, or represents cycloalkyl which has 3 to 8 carbon atoms and which is optionally monosubstituted or polysubstituted by identical or different substituents, suitable cycloalkyl substituents being: halogen, straight-chain or branched alkyl having 1 to 4 carbon atoms or straight-chain or branched halogenoalkyl having 1 to 4 carbon atoms and 1 to 9 identical or different halogen atoms, $R^2$ furthermore represents arylalkyl, aryloxyalkyl, arylthioalkyl or heteroarylalkyl, each of which has 1 to 6 carbon atoms in the straight-chain or branched alkyl moiety and each of which has 6 to 10 carbon atoms in the aryl moiety, or 2 to 9 carbon atoms and 1 to 4 hetero atoms—in particular nitrogen, oxygen and/or sulphur—in the heteroaryl moiety, and each of which is optionally monosubstituted or polysubstituted if appropriate in the aryl, or heteroaryl, moiety by identical or different substituents, suitable aryl, or heteroaryl, substituents in each case being: halogen, cyano, nitro, in each case straight-chain or branched alkyl, alkoxy or alkylthio, each of which has 1 to 4 carbon atoms, in each case straight-chain or branched halogenoalkyl, halogenoalkoxy, halogenoalkylthio, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, and phenyl which is optionally monosubstituted or polysubstituted by identical or different substituents from the series comprising halogen and/or straight-chain or branched alkyl having 1 to 4 carbon atoms, and Het represents an N-linked mono- or polyunsaturated nitrogen-containing heterocycle which has 2 to 9 carbon atoms and, if appropriate, 1 to 4 further hetero atoms—in particular nitrogen, oxygen and/or sulphur—and which is optionally monosubstituted or polysubstituted by identical or different substituents, suitable heterocyclyl substituents being those mentioned in the case of $R^2$.

Particularly preferred compounds of the formula (I) are those in which $R^1$ represents hydrogen, or represents an in each case straight-chain or branched radical from the series comprising alkyl having 1 to 10 carbon atoms, alkenyl having 2 to 5 carbon atoms, alkinyl having 2 to 5 carbon atoms, alkoxyalkyl or alkylthioalkyl, each of which has 1 to 4 carbon atoms in the individual alkyl moieties, halogenoalkyl having 1 to 4 carbon atoms and 1 to 9 identical or different halogen atoms, halogenoalkenyl having 2 to 5 carbon atoms and 1 to 9 identical or different halogen atoms, halogenoalkinyl having 2 to 5 carbon atoms and 1 to 7 identical or different halogen atoms, or represents cycloalkyl which has 3 to 7 carbon atoms and which is optionally monosubstituted to pentasubstituted by identical or different substituents, suitable cycloalkyl substituents being: halogen, straight-chain or branched alkyl having 1 to 3 carbon atoms or straight-chain or branched halogenoalkyl having 1 to 3 carbon atoms and 1 to 7 identical or different halogen atoms, $R^1$ furthermore represents arylalkyl, aryloxyalkyl, arylthioalkyl or heteroarylalkyl, each of which has 1 to 4 carbon atoms in the straight-chain or branched alkyl moiety and each of which has 6 or 10 carbon atoms in the aryl moiety, or 2 to 9 carbon and 1 to 3 hetero atoms—in particular nitrogen, oxygen and/or sulphur—in the heteroaryl moiety, and each of which is optionally monosubstituted to pentasubstituted if appropriate in the aryl, or heteroaryl, moiety by identical or different substituents, suitable aryl, or heteroaryl, substituents in each case being: halogen, cyano, nitro, in each case straight-chain or branched alkyl, alkoxy or alkylthio, each of which has 1 to 3 carbon atoms, in each case straight-chain or branched halogenoalkyl, halogenoalkoxy, halogenoalkylthio, each of which has 1 to 2 carbon atoms and 1 to 5 identical or different halogen atoms, in each case straight-chain or branched alkoxycarbonyl or alkoximinoalkyl, each of which has 1 to 3 carbon atoms in the individual alkyl moieties, and phenyl which is optionally monosubstituted to pentasubstituted by identical or different substituents from the series comprising halogen and/or straight-chain or branched alkyl having 1 to 3 carbon atoms, $R^2$ represents an in each case straight-chain or branched radical from the series comprising alkyl, alkoxy or alkylthio, each of which has 1 to 6 carbon atoms, alkenyl having 2 to 5 carbon atoms, alkinyl having 2 to 5 carbon atoms, halogenoalkyl having 1 to 4 carbon atoms and 1 to 9 identical or different halogen atoms, halogenoalkenyl having 2 to 5 carbon atoms and 1 to 9 identical or different halogen atoms, halogenoalkinyl having 2 to 5 carbon atoms and 1 to 7 identical or different halogen atoms, or represents cycloalkyl which has 3 to 7 carbon atoms and which is optionally monosubstituted to pentasubstituted by identical or different substituents, suitable cycloalkyl substituents being: halogen, straight-chain or branched alkyl having 1 to 3 carbon atoms or straight-chain or branched halogenoalkyl having 1 to 3 carbon atoms and 1 to 7 identical or different halogen atoms, $R^2$ furthermore represents arylalkyl, aryloxyalkyl, arylthioalkyl or heteroarylalkyl, each of which has 1 to 4 carbon atoms in the straight-chain or branched alkyl moiety and each of which has 6 or 10 carbon atoms in the aryl moiety, or 2 to 9 carbon atoms and 1 to 3 hetero atoms—in particular nitrogen, oxygen and/or sulphur—in the heteroaryl moiety, and each of which is optionally monosubstituted to pentasubstituted if appropriate in the aryl, or heteroaryl, moiety by identical or different substituents, suitable aryl, or heteroaryl, substituents in each case being: halogen, cyano, nitro, in each case straight-chain or branched alkyl, alkoxy or alkylthio, each of which has 1 to 3 carbon atoms, in each case straight-chain or branched halogenoalkyl, halogenoalkoxy, halogenoalkylthio, each of which has 1 to 2 carbon atoms and 1 to 5 identical or different halogen atoms, in each case straight-chain or branched alkoxycarbonyl or alkoximinoalkyl, each of which has 1 to 3 carbon atoms in the individual alkyl moieties, and phenyl which is optionally mono substituted to pentasubstituted by identical or different substituents from the series comprising halogen and/or straight-chain or branched alkyl having 1 to 3 carbon atoms, and Het represents an N-linked mono- or polyunsaturated nitrogen-containing heterocycle which has 2 to 9 carbon atoms and, if appropriate, 1 to 3 further hetero atoms—in particular nitrogen, oxygen and/or sulphur——and which is optionally monosubstituted to pentasubstituted by identical or different substituents, suitable heterocyclyl substituents being those mentioned in the case of $R^2$.

Very particularly preferred compounds of the formula (I) are those in which $R^1$ represents hydrogen, or represents an in each case straight-chain or branched radical from the series comprising alkyl having 1 to 8 carbon atoms, alkenyl having 2 to 3 carbon atoms, alkinyl having 2 to 3 carbon atoms, alkoxyalkyl or alkylthioalkyl, each of which has 1 to 3 carbon atoms in the individual alkyl moieties, halogenoalkyl having 1 or 2 carbon atoms and 1 to 5 identical or different halogen atoms, halogenoalkenyl having 2 to 3 carbon atoms and 1 to 5 identical or different halogen atoms, halogenoalkinyl having 2 to 3 carbon atoms and 1 to 3 identical or different halogen atoms, or represents cyclopropyl, cyclopentyl or cyclohexyl, each of which is optionally monosubstituted to trisubstituted by identical or different substituents, suitable substituents in each case being: fluorine, chlorine, bromine, methyl, ethyl or trifluoromethyl, $R^1$ furthermore represents phenylalkyl, phenyloxyalkyl, phenylthioalkyl or heteroarylalkyl, each of which has 1 to 2 carbon atoms in the alkyl moiety and, if appropriate, 2 to 9 carbon atoms and 1 to 3 hetero atoms—in particular nitrogen, oxygen and/or sulphur—in the heteroaryl moiety, and each of which is optionally monosubstituted to trisubstituted if appropriate in the phenyl, or heteroaryl, moiety by identical or different substituents, suitable phenyl, or heteroaryl, substituents in each case being: fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, trifluoromethoxy, trifluoromethylthio, methoxycarbonyl, ethoxycarbonyl, methoximinomethyl, methoximinoethyl, ethoximinomethyl, ethoximinoethyl, or phenyl which is optionally monosubstituted to trisubstituted by identical or different substituents from the series comprising fluorine, chlorine, bromine, methyl and/or ethyl, $R^2$ represents an in each case straight-chain or branched radical from the series comprising alkyl, alkoxy or alkylthio, each of which has 1 to 4 carbon atoms, alkenyl having 2 to 3 carbon atoms, alkinyl having 2 to 3 carbon atoms, halogenoalkyl having 1 to 2 carbon atoms and 1 to 5 identical or different halogen atoms, halogenoalkenyl having 2 to 3 carbon atoms and 1 to 5 identical or different halogen atoms, halogenoalkinyl having 2 to 3 carbon atoms and 1 to 3 identical or different halogen atoms, or represents cyclopropyl, cyclopentyl or cyclohexyl, each of which is optionally monosubstituted to trisubstituted by identical or different substituents, suitable substituents in each case being: fluorine, chlorine, bromine, methyl, ethyl or trifluoromethyl, $R^2$ furthermore represents phenylalkyl, phenyloxyalkyl, phenylthioalkyl or heteroarylalkyl, each of which has 1 to 2 carbon atoms in the straight-chain or branched alkyl moiety and, if appropriate, 2 to 9 carbon atoms and 1 to 3 hetero atoms—in particular nitrogen, oxygen and/or sulphur—in the heteroaryl moiety, and each of which is optionally monosubstituted to trisubstituted if appropriate in the phenyl, or heteroaryl, moiety by identical or different substituents, suitable phenyl, or heteroaryl, substituents in each case being: fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, trifluoromethoxy, trifluoromethylthio, methoxycarbonyl, ethoxycarbonyl, methoximinomethyl, methoximinoethyl, ethoximinomethyl, ethoximinoethyl, or phenyl which is optionally monosubstituted to trisubstituted by identical or different substituents from the series comprising fluorine, chlorine, bromine, methyl and/or ethyl, and Het represents pyrazolyl, pyrrolyl, imidazolyl, triazolyl, tetrazolyl, indolyl, indazolyl or benzimidazolyl, each of which is N-linked and each of which is optionally monosubstituted to trisubstituted by identical or different substituents, suitable heterocyclyl substituents in each case being: fluorine, chlorine, bromine, cyano, nitro, methyl, ethyl, n- or i-propyl, n-, i-, s- or t-butyl, methoxy, ethoxy, n- or i-propoxy, n-, i-, s—or t-butoxy, methylthio, ethylthio, trifluoromethyl, trifluoromethoxy, trifluoromethylthio, methoxycarbonyl, ethoxycarbonyl, methoximinomethyl, methoximinoethyl, ethoximinomethyl, ethoximinoethyl, or phenyl which is optionally monosubstituted to trisubstituted by identical or different substituents from the series comprising fluorine, chlorine, bromine, methyl and/or ethyl.

If, for example, 1-isopropyl-4-methylthio-1,3,5-(3H)-triazine-2,6-dione and imidazole are used as starting materials, the course of the reaction of process (a) according to the invention can be represented by the following equation:

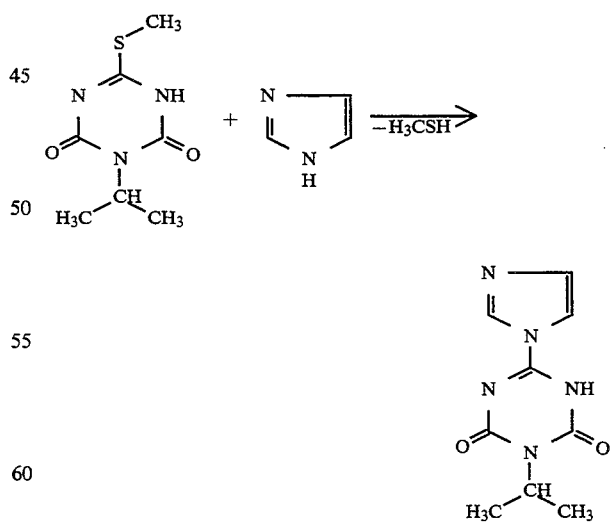

If, for example, 1-isopropyl-3-methyl-4-(1-pyrazolyl)-1,3,5-(3H)-triazine-2,6-dione and nitric acid are used as starting materials, the course of the reaction of process (b) according to the invention can be represented by the following equation:

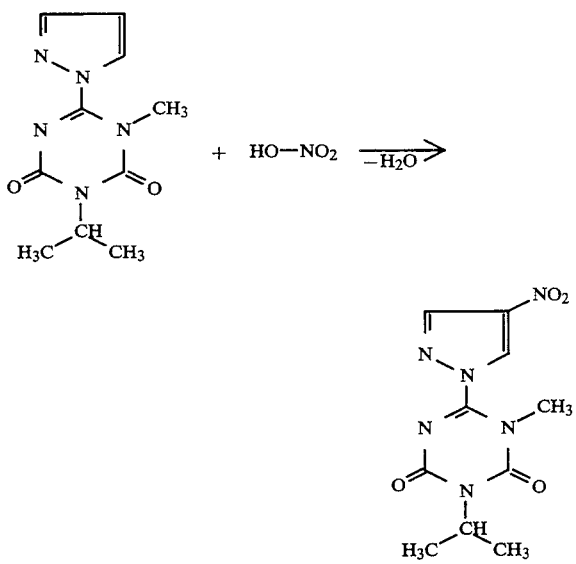

Formula (II) provides a general definition of the 4-alkylthio-triazinediones required as starting materials for carrying out process (a) according to the invention. In this formula (II), R$^1$ and R$^2$ preferably represent those radicals which have already been mentioned in connection with the description of the compounds of the formula (I) according to the invention as being preferred for this substituent.

R$^3$ preferably represents straight-chain or branched alkyl having 1 to 4 carbon atoms, in particular methyl or ethyl.

The 4-alkylthio-triazinediones of the formula (II) have been disclosed (compare, for example, GB 1,435,585).

Formula (III) provides a general definition of the heterocycles furthermore required as starting materials for carrying out process (a) according to the invention. In this formula (III), Het preferably represents those radicals which have already been mentioned in connection with the description of the substances of the formula (I) according to the invention as being preferred for this substituent.

The heterocycles of the formula (III) are generally known compounds of organic chemistry.

The electrophilic reagents furthermore required as starting materials for carrying out process (b) according to the invention are generally known compounds of organic chemistry. Suitable electrophilic reagents are, for example, halogenating agents such as sulphuryl chloride, phosphorus oxychloride, phosphorus oxybromide or phosphorus tribromide, or nitrating agents such as nitric acid or nitrating acid.

Suitable diluents for carrying out process (a) according to the invention are inert organic solvents. These include, in particular, aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform or carbon tetrachloride; ethers such as diethyl ether, diisopropyl ether, dioxane, tetrahydrofuran or ethylene glycol dimethyl ether or ethylene glycol diethyl ether; ketones such as acetone or butanone or methyl isobutyl ketone; nitriles such as acetonitrile, propionitrile or benzonitrile; amides such as N,N-dimethylformamide, N,N-dimethylacetamide, N-methylformanilide, N-methylpyrrolidone or hexamethylphosphoric triamide, esters such as methyl acetate or ethyl acetate, or organic acids such as, for example, glacial acetic acid.

When carrying out process (a) according to the invention, the reaction temperatures can be varied within a substantial range. In general, the process is carried out at temperatures between 20° C. and 200° C., preferably at temperatures between 50° C., and 150° C.

Process (a) according to the invention is customarily carried out under atmospheric pressure. However, it is also possible to carry out the process under increased or reduced pressure.

For carrying out process (a) according to the invention, 1.0 to 50.0 mol, preferably 1.0 to 10.0 mol, of heterocycle of the formula (III) is generally employed per mole of 4-alkylthio-triazinedione of the formula (II). The reaction is carried out and the reaction products are worked up and isolated by known processes (compare, in this context, also the Preparation Examples).

Diluents which can be employed for carrying out process (b) according to the invention are all solvents which can be employed for such electrophilic substitution reactions. It is preferred to use as reagents the acids or mixtures which are suitable, such as, for example, nitric acid, nitrating acid or sulphuryl chloride, simultaneously as the diluent. If appropriate, inert organic solvents such as, for example, glacial acetic acid or chlorinated hydrocarbons such as methylene chloride, chloroform or carbon tetrachloride, can also be used as diluents.

Catalysts or reaction auxiliaries for carrying out process (b) according to the invention which can be employed are also the reaction auxiliaries customary for such electrophilic substitution reactions. It is preferred to use acidic catalysts, such as for example, sulphuric acid, iron(III) chloride or other Lewis acids, or else acetic anhydride.

When carrying out process (b) according to the invention, the reaction temperatures can be varied within a substantial range. In general, the process is carried out at temperatures between −50° C. and +200° C., preferably at temperatures between −20° C. and +150° C.

Process (b) according to the invention is customarily carried out under atmospheric pressure. However, it is also possible to carry out the process under increased or reduced pressure.

For carrying out process (b) according to the invention, 1.0 to 10.0 mol, preferably 1.0 to 5.0 mol, of electrophilic reagent and, if appropriate, 0.1 to 10.0 mol of catalyst or reaction auxiliary are generally employed per mole of substituted heterocyclyltriazinedione of the formula (I).

The reaction is carried out and the reaction products are worked up and isolated by generally known processes.

The end products of the formula (I) are purified with the aid of customary processes, for example by column chromatography or by recrystallisation.

They are characterised with the aid of the melting point or, in the case of compounds which do not crystallise, with the aid of proton nuclear resonance spectroscopy ($^1$H NMR).

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial plants and railway lines, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, sports fields and pasture-land, and for the selective combating of weeds in annual cultures.

In this context, the active compounds according to the invention can be employed with particularly good success for combating monocotyledon and dicotyledon weeds in monocotyledon and dicotyledon cultures such as, for example, wheat, maize or soy beans.

Moreover, the active compounds are suitable for combating animal pests, preferably arthropods and nematodes, in particular insects and arachnids, which are encountered in agriculture, in forestry, in the protection of stored products and of materials, and in the hygiene field. They are active against normally sensitive and resistant species and against all or some stages of development.

The abovementioned pests include:

From the order of the Isopoda, for example, *Oniscus asellus*, *Armadillidium vulgare* and *Porcellio scaber*.

From the order of the Diplopoda, for example, *Blaniulus guttulatus*.

From the order of the Chilopoda, for example, *Geophilus carpophagus* and Scutigera spec.

From the order of the Symphyla, for example, *Scutigerella immaculata*.

From the order of the Thysanura, for example, *Lepisma saccharina*.

From the order of the Collembola, for example, *Onychiurus armatus*.

From the order of the Orthoptera, for example, *Blatta orientalis*, *Periplaneta americana*, *Leucophaea maderae*, *Blattella germanica*, *Acheta domesticus*, Gryllotalpa spp., *Locusta migratoria migratorioides*, *Melanoplus differentialis* and *Schistocerca gregaria*.

From the order of the Dermaptera, for example, *Forficula auricularia*.

From the order of the Isoptera, for example, Reticulitermes spp..

From the order of the Anoplura, for example, *Phylloxera vastatrix*, Pemphigus spp., *Pediculus humanus corporis*, Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci*.

From the order of the Heteroptera, for example, Eurygaster spp., *Dysdercus intermedius*, *Piesma quadrata*, *Cimex lectularius*, *Rhodnius prolixus* and Triatoma spp.

From the order of the Homoptera, for example, *Aleurodes brassicae*, *Bemisia tabaci*, *Trialeurodes vaporariorum*, *Aphis gossypii*, *Brevicoryne brassicae*, *Cryptomyzus ribis*, *Aphis fabae*, *Doralis pomi*, *Eriosoma lanigerum*, *Hyalopterus arundinis*, *Macrosiphumavenae*, Myzus spp., *Phorodon humuli*, *Rhopalosiphum padi*, Empoasca spp., *Euscelis bilobatus*, *Nephotettix cincticeps*, *Lecanium corni*, *Saissetia oleae*, *Laodelphax striatellus*, *Nilaparvata lugens*, *Aonidiella aurantii*, *Aspidiotus hederae*, Pseudococcus spp. and Psylla spp.

From the order of the Lepidoptera, for example, *Pectinophora gossypiella*, *Bupalus piniarius*, *Cheimatobia brumata*, *Lithocolletis blancardella*, *Hyponomeuta padella*, *Plutella maculipennis*, *Malacosoma neustria*, *Euproctis chrysorrhoea*, Lymantria spp. *Bucculatrix thurberiella*, *Phyllocnistis citrella*, Agrotis spp., Euxoa spp., Feltia spp., *Earias insulana*, Heliothis spp., *Spodoptera exigua*, *Mamestra brassicae*, *Panolis flammea*, *Prodenia litura*, Spodoptera spp., *Trichoplusia ni*, *Carpocapsa pomonella*, Pieris spp., Chilo spp., *Pyrausta nubilalis*, *Ephestia kuehniella*, *Galleria mellonella*, *Tineola bisselliella*, *Tinea pellionella*, *Hofmannophila pseudospretella*, *Cacoecia podana*, *Capua reticulana*, *Choristoneura fumiferana*, *Clysia ambiguella*, *Homona magnanima* and *Tortrix viridana*.

From the order of the Coleoptera, for example, *Anobium punctatum*, *Rhizopertha dominica*, *Bruchidius obtectus*, *Acanthoscelides obtectus*, *Hylotrupes bajulus*, *Agelastica alni*, *Leptinotarsa decemlineata*, *Phaedon cochleariae*, Diabrotica spp., *Psylliodes chrysocephala*, *Epilachna varivestis*, Atomaria spp., *Oryzaephilus surinamensis*, Anthonomus spp., Sitophilus spp., *Otiorrhynchus sulcatus*, *Cosmopolites sordidus*, *Ceuthorrhynchus assimilis*, *Hypera postica*, Dermestes spp., Trogoderma spp., Anthrenus spp., Attagenus spp., Lyctus spp., *Meligethes aeneus*, Ptinus spp., *Niptus hololeucus*, *Gibbium psylloides*, Tribolium spp., *Tenebrio molitor*, Agriotes spp., Conoderus spp., *Melolontha melolontha*, *Amphimallon solstitialis* and *Costelytra zealandica*.

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

The active substances according to the invention are distinguished by a powerful insecticidal activity. They can be employed with particularly good success for combating insects which damage plants such as, for example, against the black bean aphid (Aphis fabae). In this context, the active compounds according to the invention show not only protective, but also root-systemic properties.

Depending on their particular physical and/or chemical properties, the active compounds can be converted into the customary formulations, such as solutions, emulsions, suspensions, powders, foams, pastes, granules, aerosols, natural and synthetic materials impregnated with active compound, very fine capsules in polymeric substances and in coating compositions for seed, furthermore in formulations used with burning equipment such as fumigating cartridges, tins and coils and the like, and in ULV cold- and warm-mist formulations.

These formulations are produced in a known manner, for example by mixing the active compounds with extenders, that is liquid solvents, liquefied gases under pressure and/or solid carriers, optionally with the use of surface-active agents, that is emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene, or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers there are meant those liquids which are gaseous at normal temperature and under atmospheric pressure, for example aerosol propellents such as halogenohydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example ligninsulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For combating weeds, the active compounds according to the invention, when used as herbicides as such or in the form of their formulations, can also be used as mixtures with known herbicides, finished formulations or tank mixes being possible.

Suitable herbicides for the mixtures are known herbicides, for example anilides such as, for example, diflufenican and propanil; arylcarboxylic acids such as, for example, dichloropicolinic acid, dicamba and picloram; aryloxyalkanoic acids such as, for example, 2,4 D, 2,4 DB, 2,4 DP, fluroxypyr, MCPA, MCPP and triclopyr; aryloxy-phenoxy-alkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulphonylureas such as, for example, amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuronmethyl, triasulfuron and tribenuron-methyl; thiocarbamates such as, for example, butylate, cycloate, diallate, EPTC, esprocarb, molinate, prosulfocarb, thiobencarb and tri-allate; triazines such as, for example, atrazine, cyanazine, simazine, simetryn, terbutryn and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

A mixture with other known active compounds, such as fungicides, insecticides, acaricides, nematicides, bird repellants, plant nutrients and agents which improve soil structure, is also possible.

When used as herbicides, the active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

When used as herbicides the active compounds according to the invention can be applied either before or after emergence of the plants.

They can also be incorporated into the soil before sowing.

When used as herbicides, the amount of active compound used can vary within a substantial range. It depends essentially on the nature of the desired effect. In general, the amounts used are between 0.001 and 10 kg of active compound per hectare of soil surface, preferably between 0.005 and 5 kg per hectare.

When used as insecticides, the active compounds according to the invention can also exist in the form of their commercially available formulations and in the use forms, prepared from these formulations, as a mixture with other active substances such as insecticides, attractants, sterilants, acaricides, nematicides, fungicides, growth-regulating substances or herbicides. The insecticides include, for example, phosphoric esters, carbamates, carboxylic esters, chlorinated hydrocarbons, phenylureas, substances produced by microorganisms, and the like.

When used as insecticides, the active compounds according to the invention can furthermore exist, in their commercially available formulations and the use forms prepared from these formulations, as a mixture with synergists. Synergists are compounds by which an increased activity of the active compounds is achieved without it being necessary for the synergist added to be active itself.

When used as insecticides the active compound content of the use forms, prepared from the commercially available formulations, can vary within wide limits. The active compound concentration of the use forms can be from 0.0000001 up to 95% by weight of active compound, preferably between 0.0001 and 1% by weight.

They are used in a customary manner adapted to suit the use forms.

The preparation and the use of the active compounds according to the invention can be seen from the examples which follow.

PREPARATION EXAMPLES

EXAMPLE 1

(Process a)

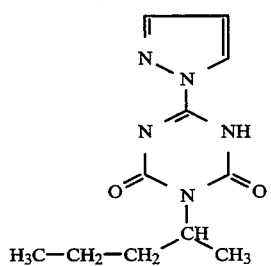

4.8 g (0.07 mol) of 1H-pyrazole are added at room temperature to 4 g (0.0175 mol) of 1-(1-methyl-1-butyl)-4-methylthio-1,3,5-(3H)-triazine-2,6-dione (compare, for example, U.S. Pat. No. 3,973,947) in 100 ml of o-dichlorobenzene, and the mixture is subsequently refluxed for one hour. For working-up, the cooled reaction mixture is diluted with dichloromethane, washed with dilute hydrochloric acid until free from pyrazole, dried over magnesium sulphate and concentrated in vacuo. The residue is recrystallised from cyclohexane.

1.8 g (41% of theory) of 1-(1-methyl-1-butyl)-4-(1-pyrazolyl)-1,3,5-(3H)-triazine-2,6-dione of melting point 99° C. to 100° C. are obtained.

The following substituted heterocyclyltriazinediones of the general formula (I) are obtained in a corresponding manner and following the general preparation instructions:

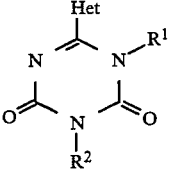

| Ex. No. | $R^1$ | $R^2$ | Het | Physical properties |
|---|---|---|---|---|
| 2 | H | i-$C_3H_7$ | 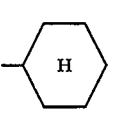 | m.p. 142° C. |
| 3 | H | cyclohexyl | 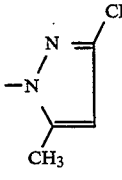 | m.p. 236° C. |
| 4 | H | i-$C_3H_7$ | 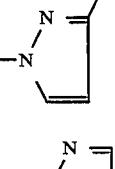 (with $CH_3$ groups) | m.p. 186° C. |
| 5 | H | i-$C_3H_7$ | 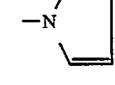 ($CH_3$) | m.p. 205° C. |
| 6 | H | n-$C_3H_7$ | 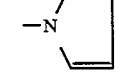 | m.p. 184° C. |
| 7 | H | $CH_3$ | 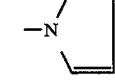 | m.p. >240° C. |
| 8 | H | n-$C_4H_9$ | 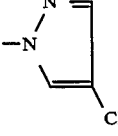 | m.p. 199° C. |
| 9 | H | i-$C_3H_7$ | (pyrazolyl with $CH_3$) | m.p. 171° C. |

-continued

![Structure I]

Het—C(=N)—N(R¹)—C(=O)—N(R²)—C(=O) (triazine ring)   (I)

| Ex. No. | R¹ | R² | Het | Physical properties |
|---|---|---|---|---|
| 10 | H | s-C₄H₉ | pyrazol-1-yl | m.p. 230° C. |
| 11 | H | —CH(CH₃)—CH(CH₃)₂ | pyrazol-1-yl | m.p. 128–129° C. |
| 12 | H | —CH₂—CH=CH₂ | pyrazol-1-yl | m.p. >230° C. |
| 13 | H | cyclopropyl | pyrazol-1-yl | m.p. 240–241° C. |
| 14 | H | C₂H₅ | pyrazol-1-yl | m.p. 194–195° C. |
| 15 | H | —CH₂—C(CH₃)₃ | pyrazol-1-yl | m.p. 197–199° C. |
| 16 | H | i-C₃H₇ | 4-Cl-pyrazol-1-yl | m.p. 87° C. |
| 17 | H | i-C₃H₇ | 4-Br-pyrazol-1-yl | m.p. 90° C. |
| 18 | H | i-C₃H₇ | 1,2,4-triazol-1-yl | m.p. 84° C. |

USE EXAMPLES

In the use examples which follow, the compound given below was employed as comparison substance:

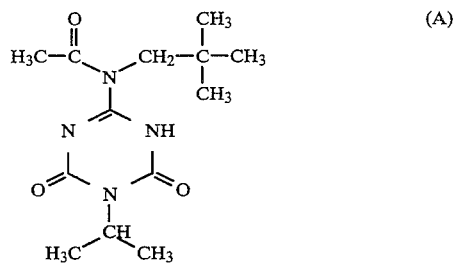

(A)

1-Isopropyl-4-[N-(2,2-dimethylpropyl) -acetamido]-1,3,5-(3H)-triazine-2,6-dione (compare, for example, DE 2,603,180).

EXAMPLE A

Post-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is chosen such that the particular amounts of active compound desired are applied in 1,000 l of water/ha. After three weeks, the degree of damage to the plants is rated in % damage in comparison to the development of the untreated control. The figures denote:

0% = no action (like untreated control)
100% = total destruction

A clearly superior activity as well as crop plant selectivity compared with the prior art is shown in this test, for example by the compound in accordance with Preparation Example 2.

EXAMPLE B

Aphis test (systemic action)
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

In each case 20 ml of preparation of active compound of the desired concentration are poured in the vicinity of bean plants (*Vicia faba*) which are heavily infested by the black bean aphid (*Aphis fabae*) in such a way that the preparation of active compound penetrates the soil without wetting the shoot. The active compound is taken up by the roots and translocated to the shoot.

After the desired period of time, the destruction is determined in %. 100% means that all aphids have been killed; 0% means that no aphid has been killed.

In this test, a superior activity compared with the prior art is shown, for example, by compound 2 of the Preparation Examples.

We claim:
1. A substituted heterocyclyltriazinedione of the formula

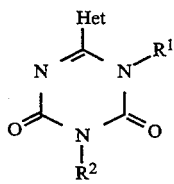

wherein
R¹ represents hydrogen, or represents a straight-chain or branched radical selected from the group consisting of alkyl having 1 to 10 carbon atoms, alkenyl having 2 to 5 carbon atoms, alkinyl having 2 to 5 carbon atoms, alkoxyalkyl or alkylthioalkyl, each of which has 1 to 4 carbon atoms in the individual alkyl moieties, halogenoalkyl having 1 to 4 carbon atoms and 1 to 9 identical or different halogen atoms, halogenoalkenyl having 2 to 5 carbon atoms and 1 to 9 identical or different halogen atoms, halogenoalkinyl having 2 to 5 carbon atoms and 1 to 7 identical or different halogen atoms, or represents cycloalkyl which has 3 to 7 carbon atoms and which is optionally monosubstituted to pentasubstituted by identical or different substituents selected from the group consisting of halogen, straight-chain or branched alkyl having 1 to 3 carbon atoms and straight-chain or branched halogenoalkyl having 1 to 3 carbon atoms and 1 to 7 identical or different halogen atoms, or R¹ furthermore represents arylalkyl, aryloxyalkyl, arylthioalkyl or heteroarylalkyl, each of which has 1 to 4 carbon atoms in the straight-chain or branched alkyl moiety and each of which has 6 or 10 carbon atoms in the aryl moiety, or 2 to 9 carbon and 1 to 3 hetero atoms in the heteroaryl moiety, and each of which is optionally monosubstituted to pentasubstituted in the aryl, or heteroaryl, moiety by identical or different substituents selected from the group consisting of halogen, cyano, nitro, straight-chain or branched alkyl, alkoxy or alkylthio, each of which has 1 to 3 carbon atoms, in each case straight-chain or branched halogenoalkyl, halogenoalkoxy or halogenoalkylthio, each of which has 1 to 2 carbon atoms and 1 to 5 identical or different halogen atoms, straight-chain or branched alkoxycarbonyl or alkoximinoalkyl, each of which has 1 to 3 carbon atoms in the individual alkyl moieties, and phenyl which is optionally monosubstituted to pentasubstituted by identical or different substituents selected from the group consisting of halogen and straight-chain or branched alkyl having 1 to 3 carbon atoms, and R² represents a straight-chain or branched radical selected from the group consisting of alkyl, alkoxy or alkylthio, each of which has 1 to 6 carbon atoms, alkenyl having 2 to 5 carbon atoms, alkinyl having 2 to 5 carbon atoms, halogenoalkyl having 1 to 4 carbon atoms and 1 to 9 identical or different halogen atoms, halogenoalkenyl having 2 to 5 carbon atoms and 1 to 9 identical or different halogen atoms and halogenoalkinyl having 2 to 5 carbon atoms and 1 to 7 identical or different halogen atoms, or represents cycloalkyl which has 3 to 7 carbon atoms and which is optionally monosubstituted to pentasubstituted by identical or different substituents selected from the group consisting of halogen, straight-chain or branched alkyl having 1 to 3 carbon atoms and straight-chain or branched halogenoalkyl having 1 to 3 carbon atoms and 1 to 7 identical or different halogen atoms, or R² furthermore represents arylalkyl, aryloxyalkyl, arylthioalkyl or heteroarylalkyl, each of which has 1 to 4 carbon atoms in the straight-chain or branched alkyl moiety and each of which has 6 to 10 carbon atoms in the aryl moiety, or 2 to 9 carbon atoms and 1 to 3 hereto atoms in the heteroaryl moiety, the aryl moiety being optionally monosubstituted to pentasubstituted by identical or different substituents selected from the group consisting of halogen, cyano, nitro, in each case straight-chain or branched alkyl, alkoxy or alkylthio, each of which has 1 to 3 carbon atoms, straight-chain or branched halogenoalkyl, halogenoalkoxy, halogencalkylthio, each of which has 1 to 2 carbon atoms and 1 to 5 identical or different halogen atoms, straight-chain or branched alkoxycarbonyl or alkoximinoalkyl, each of which has 1 to 3 carbon atoms in the individual alkyl moieties, and phenyl which is optionally monosubstituted to pentasubetituted by identical or different substituents selected from the group consisting of halogen and straight-chain or branched alkyl having 1 to 3 carbon atoms, and Het and heteroaryl of the heteroarylalkyl radicals represent pyrazolyl, imidazolyl, triazolyl, tetrazolyl, indolyl, indazolyl or benzimidazolyl, each of which is N-linked and each of which is optionally monosubstituted to trisubstituted by identical or different substituents selected from the group consisting of fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, trifluoromethoxy, trifluoro-methylthio, methoxycarbonyl, ethoxycarbonyl, methoximinomethyl, methoximinoethyl, ethoximinomethyl, ethoximinoethyl, and phenyl which is optionally monosubstituted to trisubstituted by identical or different substituents selected from the group consisting of fluorine, chlorine, bromine, methyl and ethyl.

2. A substituted heterocyclyltriazinedione according to claim 1, wherein
R¹ represents hydrogen, or represents an in each case straight-chain or branched radical selected from the group consisting of alkyl having 1 to 8 carbon atoms, alkenyl having 2 to 3 carbon atoms, alkinyl having 2 to 3 carbon atoms, alkoxyalkyl or alkylthioalkyl, each of which has 1 to 3 carbon atoms in the individual alkyl moieties, halogenoalkyl having 1 to 2 carbon atoms and 1 to 5 identical or different halogen atoms, halogenoalkenyl having 2 to 3 carbon atoms and 1 to 5 identical or different halogen atoms, halogenoalkinyl having 2 to 3 carbon atoms and 1 to 3 identical or different halogen atoms, or represents cyclopropyl, cyclopentyl or cyclohexyl, each of which is optionally monosubstituted to trisubstituted by identical or different substituents selected from the group consisting of fluorine, chlorine, bromine, methyl, ethyl and trifluoromethyl, or R¹ furthermore represents phenylalkyl, phenyloxyalkyl, phenylthioalkyl or heteroarylalkyl, each of which has 1 to 2 carbon atoms in the alkyl moiety, the alkyl moiety being optionally monosubstituted to trisubstituted by identical or different substituents selected from the group consisting of fluorine, chlorine, bromine, cyano, nitro, methyl, ethyl, n- or i-propyl, n-, i-, s- or t-butyl, methoxy, ethoxy, n- or i-propyl, n-, i-, s- or t-butoxy, methylthio, ethylthio, trifluoromethyl, trifluoromethoxy, trifluoromethylthio, methoxycarbonyl, ethoxycarbonyl, methoximinomethyl, methoximinoethyl, ethoximinomethyl, ethoximinoethyl and phenyl which is optionally monosubstituted to trisubstituted by identical or different substituents selected from the group consisting of fluorine, chlorine, bromine, methyl and ethyl, and R² represents straight-chain or branched radical selected from the group consisting of alkyl, alkoxy or alkylthio, each of which has 1 to 4 carbon atoms, alkenyl having 2 to 3 carbon atoms, alkinyl having 2 to 3 carbon atoms, halogenoalkyl having 1 to 2 carbon atoms and 1 to 5 identical or different halogen atoms, halogenoalkenyl having 2 to 3 carbon atoms and 1 to 5 identical or different halogen atoms, and halogenoalkinyl having 2 to 3 carbon atoms and 1 to 3 identical or different halogen atoms, or represents cyclopropyl, cyclopentyl or cyclohexyl, each of which is optionally monosubstituted to trisubstituted by identical or different substituents selected from the group consisting of fluorine, chlorine, bromine, methyl, ethyl and trifluoromethyl, or R² furthermore represents phenylalkyl, phenyloxyalkyl, phenylthioalkyl or heteroarylalkyl, each of which has 1 to 2 carbon atoms in the straight-chain or branched alkyl moiety and each of which is optionally monosubstituted to trisubstituted in the phenyl moiety by identical or different substituents selected from the group consisting of fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, trifluoromethoxy, trifluoromethylthio, methoxycarbonyl, ethoxycarbonyl, methoximinomethyl, methoximinoethyl, ethoximinomethyl, ethoximinoethyl, and phenyl which is optionally monosubstituted to trisubstituted by identical or different substituents selected from the group consisting of fluorine, chlorine, bromine, methyl and ethyl, and Het and heteroaryl of the heteroarylalkyl moieties represent pyrazotyl, imidazolyl, triazolyl, tetrazolyl, indolyl, indazolyl or benzimidazolyl, each of which is N-linked and each of which is optionally monosubstituted to trisubstituted by identical or different substituents selected from the group consisting of fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, trifluoromethoxy, trifluoromethylthio, methoxycarbonyl, ethoxycarbonyl, methoximinomethyl, methoximinoethyl, ethoximinomethyl, ethoximinoethyl, and phenyl which is optionally monosubstituted to trisubstituted by identical or different substituents selected from the group consisting of fluorine, chlorine, bromine, methyl and ethyl.

3. A compound according to claim 1, wherein such compound is 1-isopropyl-4-(1-pyrazolyl)-1,3,5-(3H)-triazine-2,6-dione of the formula

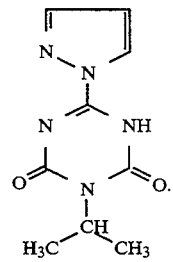

4. A compound according to claim 1, wherein such compound is 1-sec.butyl-4-(1-pyrazolyl)-1,3,5-(3H)-triazine-2,6-dione of the formula

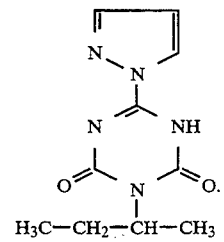

5. A compound according to claim 1, wherein such compound is 1-(1-methyl-1-isobutyl)-4-(1-pyrazolyl)-1,3,5-(3H)-triazine-2,6-dione of the formula

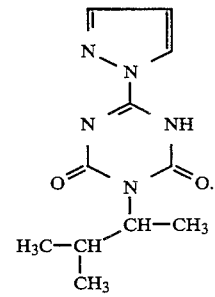

6. A compound according to claim 1, wherein such compound is 1-allyl-4-(1-pyrazolyl)-1,3,5-(3H)-triazine-2,6-dione of the formula

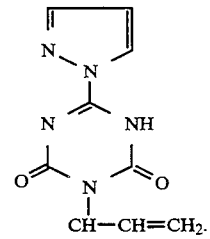

7. A compound according to claim 1, wherein such compound is 1-ethyl-4-(1-pyrazolyl)-1,3,5-(3H)-triazine-2,6-dione of the formula

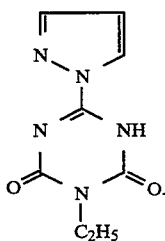

8. A herbicidal composition comprising a herbicidally effective amount of a compound according to claim 1 and a diluent.

9. A method of combating unwanted vegetation which comprises applying to such vegetation or to a locus from which it is desired to exclude such vegetation a herbicidally effective amount of a compound according to claim 1.

10. The method according to claim 9, wherein such compound is
1-isopropyl-4-(1-pyrazolyl)-1,3,5-(3H)-triazine-2,6-dione
1-sec-butyl-4-(1-pyrazolyl)-1,3,5-(3H)-triazine-2,6-dione
1-(1-methyl-1-isobutyl)-4-(1-pyrazolyl)-1,3,5-(3H)-triazine-2, 6-dione
1-allyl-4-(1-pyrazolyl)-1,3,5-(3H)-triazine-2,6-dione
1-ethyl-4-(1-pyrazolyl)-1,3,5-(3H)-triazine-2,6-dione.

11. A substituted heterocyclyltriazinedione according to claim 1, wherein Het is pyrazolyl.

* * * * *

UNITED STATES PATENT AND TRADEMARK OFFICE
CERTIFICATE OF CORRECTION

PATENT NO.    : 5,389,599
DATED         : February 14, 1995
INVENTOR(S)   : Schallner, et al.

It is certified that error appears in the above-indentified patent and that said Letters Patent is hereby corrected as shown below:

Col. 18, line 24    Delete " halogencalkylthio " and substitute -- halogenoalkylthio --

Col. 19, line 55    Delete " pyrazotyl " and substitute -- pyrazolyl --

Signed and Sealed this

Twenty-fifth Day of April, 1995

Attest:

BRUCE LEHMAN

*Attesting Officer*    *Commissioner of Patents and Trademarks*